(12) United States Patent
Adams et al.

(10) Patent No.: US 8,952,017 B2
(45) Date of Patent: Feb. 10, 2015

(54) ACYCLOVIR FORMULATIONS

(71) Applicant: Emisphere Technologies, Inc., Roseland, NJ (US)

(72) Inventors: Amy C. Adams, Roseland, NJ (US); Brahma N. Singh, Roseland, NJ (US); Nikhil Dhoot, Dombivlli (IN); Shingai Majuru, Brewster, NY (US)

(73) Assignee: Emisphere Technologies, Inc., Roseland, NJ (US)

( * ) Notice: Subject to any disclaimer, the term of this patent is extended or adjusted under 35 U.S.C. 154(b) by 0 days.

(21) Appl. No.: 13/839,936

(22) Filed: Mar. 15, 2013

(65) Prior Publication Data

US 2013/0281471 A1 Oct. 24, 2013

Related U.S. Application Data

(63) Continuation of application No. 11/568,826, filed as application No. PCT/US2005/017815 on May 19, 2005, now abandoned.

(60) Provisional application No. 60/573,003, filed on May 19, 2004.

(51) Int. Cl.
*A01N 43/90* (2006.01)
*A61K 31/522* (2006.01)
*A61K 47/18* (2006.01)
*A61K 9/00* (2006.01)
*A61K 9/08* (2006.01)
*A61K 9/20* (2006.01)
*A61K 47/12* (2006.01)

(52) U.S. Cl.
CPC .............. *A61K 47/18* (2013.01); *A61K 9/0019* (2013.01); *A61K 9/08* (2013.01); *A61K 9/2013* (2013.01); *A61K 31/522* (2013.01); *A61K 47/12* (2013.01)
USPC .................................................. 514/263.38

(58) Field of Classification Search
None
See application file for complete search history.

(56) References Cited

U.S. PATENT DOCUMENTS

| 4,199,574 A | 4/1980 | Schaeffer |
| 5,384,333 A | 1/1995 | Davis et al. |
| 5,883,103 A * | 3/1999 | Burnside et al. ......... 514/263.38 |
| 2003/0017189 A1 * | 1/2003 | Wong et al. ................... 424/426 |
| 2005/0277621 A1 | 12/2005 | Gschneidner |

FOREIGN PATENT DOCUMENTS

| WO | WO-9640144 A1 | 12/1996 |
| WO | WO-9736480 A1 | 10/1997 |
| WO | WO-0059863 A1 | 10/2000 |
| WO | WO-0220466 A1 | 3/2002 |
| WO | WO 2004/024126 * | 3/2004 |
| WO | WO-2004024216 A1 | 3/2004 |
| WO | WO-2004104018 A2 | 12/2004 |

OTHER PUBLICATIONS

Aungst (Journal of Pharmaceutical Sciences vol. 89, No. 4, 429-442 Apr. 2000 (published online Mar. 22, 2000)).*
Dörwald, F. Zaragoza. Side Reactions in Organic Synthesis: A Guide to Successful Synthesis Design, Weinheim: Wiley-VCH Verlag GmbH & Co. KGaA, 2005, Preface).*
Jordan, V. C. (Nature Reviews: Drug Discovery, 2, 2003, 205-213).*
Park et al. (Pharmaceutical Research, vol. 9, No. 10, 1992).*
Shoei et al. "Transbuccal Delivery of Acyclovir (II): Feasibility, System Design, and In Vitro Permeation Studies" J Pharm Pharmaceut Sci (www.ualberta.ca/~csps) 1 (2):66-73, 1998.*
Aungst, et al., Intestinal Permeating Enhancers, Journal of Pharmaceutical Sciences, 89:4:429-442.
Yamazaki, et al., abstract only, The Effect of Fatty Acids on the Rectal Absorpotion of Acyclovir in Rats, J. Pharm Pharmacol., Jun. 1990, 42:6:1-3.
Extended European Search Report issued in EP05751979 on Nov. 3, 2010.
International Search Report issued in PCT/US05/17815 on Oct. 31, 2005.

* cited by examiner

*Primary Examiner* — Jeffrey S Lundgren
*Assistant Examiner* — William Lee
(74) *Attorney, Agent, or Firm* — Blank Rome LLP (57) ABSTRACT

The present invention relates to an acyclovir formulation having improved bioavailability resulting in better efficacy and/or requiring less frequent administration.

11 Claims, 10 Drawing Sheets

ACYCLOVIR FORMULATIONS

This application is a continuation of U.S. patent application Ser. No. 11/568,826, filed Nov. 19, 2007, which is the U.S. national phase of International Patent Application No. PCT/US2005/17815, filed May 19, 2005, which claims the benefit of U.S. Provisional Application No. 60/753,003, filed May 19, 2004, which is hereby incorporated by reference.

FIELD OF THE INVENTION

The present invention relates to an acyclovir formulation having improved bioavailability resulting in improved efficacy and or requiting less frequent administration.

BACKGROUND OF THE INVENTION

Acyclovir (9((2-hydroxyethoxy)methyl)guanine) is an antiviral which inhibits human herpes viruses, including herpes simplex types 1 (HSV-1) and 2 (HSV-2), varicella zoster, Epstein-Barr virus (EBV) and cytomegalovirus (CMV). The inhibitory activity of acyclovir is highly selective for these viruses. O'Brien and Campoli-Richards, *Drugs*, 37:233-309 (1989). The chemical composition of acyclovir is reported in Shaffer, et al. (*J. Med. Chem.* 14:367 (1971)), U.S. Pat. No. 4,199,574, and UK Patent Specification No. 1,523,865, all of which are hereby incorporated by reference.

Acyclovir has been demonstrated to be a potent antiviral agent, particularly against herpes viruses. Shaffer, et al. *Nature* 272:583-585 (1978). Acyclovir has also been demonstrated to effectively suppress reactivated or newly acquired viral diseases such as genital herpes simplex, shingles, and varicella-zoster, as well as acute varicella-zoster infections. Balfour, *J. Med. Virology*, S1:74-81 (1993). Morbidity and mortality from viral disease have been reduced by pre- and postoperative prophylaxis with long-term (>6 months) oral acyclovir therapy. Prentice et al., *Lancet* 343:749-753 (1994). Concurrent acyclovir and AZT (azidothymidine) therapy has extended the survival of AIDS patients by one year when acyclovir therapy was begun at time of diagnosis. Stein, et al., *Ann. Intern. Med.* 121:100-108 (1994). Additionally, acyclovir therapy for acute varicella-zoster disease reduces fever, chronic pain, and the progression of rash and accelerates cutaneous healing.

Other uses include, but are not limited, to, mucocutaneous, ocular, and systemic herpes simplex infections (HSV), including in human immunodeficiency virus (HIV)-infected individuals. It is also useful to treat HSV encephalitis, neonatal HSV infections, and genital herpes (first episode, recurrent and suppressive therapy for recurrent infections). Further, acyclovir is effective therapy for varicella-zoster infections, herpes zoster (shingles, zoster), cytomegalovirus infections, infections and disorders associated with Epstein-Barr virus, and the Center for Disease Control states that oral acyclovir may be used in pregnant women. These and other uses are found in *AHFS Drug Information*, American Society of Health System Pharmacists, Bethesda, Md., 2005, which is incorporated by reference herein.

Acyclovir, is currently marketed as capsules, tablets and suspension for oral administration. Orally administered acyclovir is slowly and erratically absorbed with 15-30% bioavailability. Barnhart (ed.), *Physicians' Desk Reference*, Oradell, N.J.: Medical Economics Data (1994). Over half the dose of the currently marketed formulation is recovered in the feces. Schaeffer at al., *Nature*, 272:583-585 (1978). Failure to respond to acyclovir therapy may arise from an inadequate dose (frequency of dose or total daily dose); patient noncompliance; malabsorption in the intestine; or, resistant viral strains. Mindel, *J. Med. Virology*, S1:39-44 (1993). The need for readily absorbed oral antiviral agents has been identified as imperative for treatment of viral diseases to both patient populations since long term IV treatment is restrictive and compliance with currently available oral acyclovir formulations is difficult. Katlama, *J. Med. Virology* S1:128-133 (1993). An acyclovir preparation for oral delivery which permitted lower dosing and less frequent administration would facilitate compliance.

Previous attempts have been made to improve the oral delivery of acyclovir. U.S. Pat. No. 5,629,016, which is hereby incorporated, by reference, discloses water dispersible tablets containing acyclovir which facilitates the ingestion of large doses (i.e. up to 800 mg) of acyclovir. The tablets, however, do not improve the bioavailability of the acyclovir.

U.S. Pat. No. 5,883,103 discloses a microemulsion system for the oral delivery of acyclovir. The system includes a water-in-oil emulsion with acyclovir dispersed in aqueous phase droplets. The droplets have an average droplet size of 20-40 nanometers and are uniformly dispersed in the continuous oil phase.

Although, previous attempts have been made to improve the delivery and bioavailability of acyclovir, these attempts have had limited success. Therefore, there is a need for oral acyclovir formulations having increased bioavailability.

SUMMARY OF THE INVENTION

The present invention provides a composition (e.g., a pharmaceutical composition) comprising (a) at least one delivery agent compound and (b) acyclovir or a salt, ester, or prodrug thereof. Preferably, the composition includes a therapeutically effective amount of acyclovir and the delivery agent compound. The composition of the present invention facilitates the delivery of acyclovir and increases its bioavailability compared to administration without the delivery agent compound. The composition is particularly well suited for oral administration. Preferably, the composition provides bioavailability (i.e., AUC) substantially equivalent to the current acyclovir formulations marketed as Zovirax® (U.S. FDA NDA No. 18828, 19909, or 20089) when:

(1) 200, 400, or 800 mg of acyclovir is administered every 4 hours 5 times daily, (2) 400 mg of acyclovir is administered 2 times daily, (3) 200 mg of acyclovir is administered 3 times daily, (4) 200 mg of acyclovir is administered 4 times daily, or (5) 200 mg of acyclovir is administered 5 times daily.

Preferred delivery agent compounds include, but are not limited to, N-(8-[2-hydroxybenzoyl]amino)caprylic acid, N-(10-[2-hydroxybenzoyl]amino)decanoic acid, 4-[(4-chloro-2-hydroxy-benzoyl)amino]butanoic acid (also known as 4-[(2-hydroxy-4-chlorobenzoyl)amino]butanoate), 8-(N-2-hydroxy-5-chlorobenzoyl)aminocaptylic acid, 8-(N-2-hydroxy-4-methoxybenzoyl)-amino-caprylic acid, and salts (e.g., pharmaceutically acceptable salts) thereof, and solvates and hydrates thereof. The salt can be, for example, a sodium salt, such as a monosodium or disodium salt.

In one embodiment, the composition comprises acyclovir or a salt, ester, or prodrug thereof and at least one delivery agent of the following structure or a salt (e.g., a pharmaceutically acceptable salt) thereof:

Formula A $$2OH-Ar-\overset{O}{\underset{\|}{C}}-\overset{R^8}{\underset{|}{N}}-R^7-\overset{O}{\underset{\|}{C}}-OH$$

wherein
Ar is phenyl or naphthyl;
Ar is optionally substituted with one or more of —OH, halogen, $C_1$-$C_4$ alkyl, $C_1$-$C_4$ alkenyl, $C_1$-$C_4$ alkoxy or $C_1$-$C_4$ haloalkoxy;
$R^7$ is $C_4$-$C_{20}$ alkyl, $C_4$-$C_{20}$ alkenyl, phenyl, naphthyl, ($C_1$-$C_{10}$ alkyl) phenyl, ($C_1$-$C_{10}$ alkenyl)phenyl, ($C_1$-$C_{10}$ alkyl)naphthyl, ($C_1$-$C_{10}$ alkenyl)naphthyl, phenyl($C_1$-$C_{10}$ alkyl), phenyl($C_1$-$C_{10}$ alkenyl), naphthyl($C_1$-$C_{10}$ alkyl), or naphthyl($C_1$-$C_{10}$ alkenyl);
$R^8$ is hydrogen, $C_1$ to $C_4$ alkyl, $C_2$ to $C_4$ alkenyl, $C_1$ to $C_4$ alkoxy, or $C_1$-$C_4$ haloalkoxy;
$R^6$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, —$CO_2R^9$, or any combination thereof;
$R^9$ is hydrogen, $C_1$ to $C_4$ alkyl, or $C_2$ to $C_4$ alkenyl; and
$R^7$ is optionally interrupted by oxygen, nitrogen, sulfur or any combination thereof. According to one embodiment, the compounds are not substituted with an amino group in the position alpha to the acid group.

In another embodiment, the composition comprises acyclovir or a salt, ester, or prodrug thereof and at least one delivery agent of the following structure or a salt (e.g., a pharmaceutically acceptable salt) thereof:

Formula B wherein
$R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —$NO_2$, —$NR^9R^{10}$, or —$N^+R^9R^{10}R^{11}(R^{12})^-$;
$R^5$ is H, —OH, —$NO_2$, halogen, —$CF_3$, —$NR^{14}R^{15}$, —$N^+R^{14}R^{15}R^{16}(R^{13})^-$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;
$R^5$ is optionally substituted with halogen, —OH, —SH, or —COOH;
$R^5$ is optionally interrupted by O, N, S, or —C(O)—;
$R^6$ is a $C_1$-$C_{12}$ alkylene, $C_2$-$C_{12}$ alkenylene, or arylene;
$R^6$ is optionally substituted with a $C_1$-$C_4$ alkyl, $C_2$-$C_4$ alkenyl, $C_1$-$C_4$ alkoxy, —OH, —SH, halogen, —$NH_2$, or —$CO_2R^8$;
$R^6$ is optionally interrupted by O or N;
$R^7$ is a bond or arylene;
$R^7$ is optionally substituted with —OH, halogen, —C(O)$CH_3$, —$NR^{10}R^{11}$, or —$N^+R^{10}R^{11}R^{12}(R^{13})^-$;
each occurrence of $R^8$ is independently H, $C_1$-$C_4$ alkyl, $C_2$-$C_4$ alkenyl, or —$NH_2$;
$R^9$, $R^{10}$, $R^{11}$, and $R^{12}$ independently H or $C_1$-$C_{10}$ alkyl;
$R^{13}$ is a halide, hydroxide, sulfate, tetrafluoroborate, or phosphate;

$R^{14}$, $R^{15}$ and $R^{16}$ are independently $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, or —C(O)$R^{17}$;
$R^{17}$ is —OH, $C_1$-$C_{10}$ alkyl, or $C_2$-$C_{12}$ alkenyl; and
$R^{18}$ is H, $C_1$-$C_6$ alkyl, —OH, —$NR^{14}R^{15}$, or $N^+R^{14}R^{15}R^{16}(R^{13})^-$.

Optionally, when $R^1$, $R^2$, $R^3$, $R^4$, and $R^5$ are H, and $R^7$ is a bond then $R^6$ is not a $C_1$-$C_6$, $C_9$ or $C_{10}$ alkyl.
Optionally, when $R^1$, $R^2$, $R^3$, and $R^4$ are H, $R^5$ is —OH, $R^7$ is a bond then $R^6$ is not a $C_1$-$C_3$ alkyl.
Optionally, when at least one of $R^1$, $R^2$, $R^3$, and $R^4$ is not H, $R^5$ is —OH, $R^7$ is a bond, then $R^6$ is not a $C_1$-$C_4$ alkyl.
Optionally, when $R^1$, $R^2$, and $R^3$ are H, $R^4$ is —$OCH_3$, $R^5$ is —C(O)$CH_3$, and $R^6$ is a bond then $R^7$ is not a $C_3$ alkyl.
Optionally, when $R^1$, $R^2$, $R^4$, and $R^5$ are H, $R^3$ is —OH, and $R^7$ is a bond then $R^6$ is not a methyl.

In yet another embodiment the composition comprises acyclovir or a salt, ester, or prodrug thereof and at least one delivery agent of the following structure or a salt (e.g., a pharmaceutically acceptable salt) thereof:

Formula C wherein
$R^1$, $R^2$, $R^3$, $R^4$ and $R^5$ are independently H, —CN, —OH, —$OCH_3$, or halogen, at least one of $R^1$, $R^2$, $R^3$, $R^4$ and $R^5$ being —CN; and
$R^6$ is a $C_1$-$C_{12}$ linear or branched alkylene, alkenylene, arylene, alkyl(arylene) or aryl(alkylene).

According to one embodiment, when $R^1$ is —CN, $R^4$ is H or —CN, and $R^2$, $R^3$, and $R^5$ are H, then $R^6$ is not methylene (($CH_2$)$_1$).

Also provided is a dosage unit form (e.g., an oral dosage unit form) comprising the composition of the present invention. The dosage unit form may be in the form of a liquid or a solid, such as a tablet, capsule or particle, including a powder or sachet.

Another embodiment is a method for administering acyclovir or a salt, ester, or prodrug thereof to an animal (preferably a mammal and more preferably a human) in need thereof, by administering the composition or dosage unit form(s) of the present invention to the animal. The preferred route of administration is oral.

Yet another embodiment is a method of treating conditions or disorders caused by a virus in an animal (preferably a mammal and more preferably a human) in need thereof by administering an effective amount of the composition or dosage unit form(s) of the present invention to the animal. In other words, an effective amount of the delivery agent compound to facilitate the delivery of the acyclovir or a salt, ester, or prodrug thereof and an effective amount (e.g., a therapeutically effective amount) of acyclovir is administered.

Yet another embodiment is a method for treating conditions or disorders caused by a virus in an animal (preferably a mammal and more preferably a human) by administering to the animal a therapeutically effective amount of the composition or dosage unit form(s) of the present invention. Such conditions and disorders, include but are not limited to, those caused by viruses of the herpes family, for example, herpes simplex 1 and 2 viruses (HSV 1 and HSV 2), varicella roster virus (VZV), cytomegalovirus (CMV), Epstein-Barr virus (EBV), and other herpes virus infections (e.g. feline herpes virus infections).

Another embodiment is a method of treating virus infections, especially herpes infections such as herpes simplex 1 and 2 viruses (HSV 1, HSV 2), varicella roster virus (VZV), cytomegalovirus (CMV) and Epstein-Barr virus (EBV), and other herpes virus infections (e.g. feline herpes virus infections) in a human or non-human animal by administering an effective amount of the composition or dosage unit form of the present invention.

Yet another embodiment is a method of treating clinical conditions or symptoms which are caused by the viruses enumerated above, including herpetic karatitis, herpetic encaphalitis, cold sores and genital infections (caused by herpes simplex), chicken pox and shingles (caused by varicella roster) and CMV-pneumonia and retinitis, particularly in immunocompromised patients including renal and bone marrow transplant patients and patients with Acquired Immune Deficiency Syndrome (AIDS) by administering an effective amount of the composition or dosage unit four of the present invention. Epstein-Barr virus (EVB) causes infectious mononucleosis, and is also suggested as the causative agent of nasopharyngeal cancer, immunoblastic lymphoma, Burkitt's lymphoma and hairy leukoplakia.

Yet another embodiment is a method of treating viral infections in an animal (preferably a mammal and more preferably a human) in need thereof by administering to the animal a therapeutically effective amount of the composition or dosage unit form(s) of the present invention. Generally, the viral infections are those treatable with acyclovir or a salt, ester, or prodrug thereof.

Yet another embodiment is a method for acute treatment of herpes zoster (also known as shingles) in a human in need thereof by administering (preferably orally) an effective amount of the pharmaceutical composition of the present invention. Preferably, the pharmaceutical composition is orally administered every 5 or more hours and less than 5 times daily. Preferably, the pharmaceutical composition provides bioavailability (i.e., AUC) substantially equivalent to the current acyclovir formulations marketed as Zovirax® (U.S. FDA NDA No. 18828, 19909, or 20089) when 200 mg of acyclovir is administered, every 4 hours 5 times daily. The treatment may be continued for 7 to 10 days.

Yet another embodiment is a method for treatment of initial episodes and/or the management of recurrent episodes of genital herpes in a human in need thereof by administering (preferably orally) an effective amount of the pharmaceutical composition of the present invention. Preferably for the treatment of initial genetic herpes, the pharmaceutical composition (e.g., 400 mg of acyclovir or a molar equivalent of a salt or prodrug thereof) is administered every 5 or more hours and less than 5 times daily. The treatment may be continued for 10 days. Preferably, the pharmaceutical composition provides bioavailability (i.e., AUC) substantially equivalent to the current acyclovir formulations marketed as Zovirax® (U.S. FDA NDA No. 18828, 19909, or 20089) when 800 mg of acyclovir is administered every 4 hours 5 times daily.

Preferably for chronic suppressive therapy for recurrent genital herpes, the composition is administered once daily or less frequently. The treatment may be continued for up to 12 months, followed by re-evaluation. Preferably, the composition provides bioavailability (i.e., AUC) substantially equivalent to the current acyclovir formulations marketed as Zovirax® (U.S. FDA NDA No. 18828, 19909, or 2.0089) when:

(1) 400 mg of acyclovir is administered 2 times daily,
(2) 200 mg of acyclovir is administered 3 times daily,
(3) 200 mg of acyclovir is administered 4 times daily, or
(4) 200 mg of acyclovir is administered 5 times daily.

Treatment may be continued for up to 12 months, followed by re-evaluation.

Yet another embodiment is a method for treatment of chickenpox in a human in need thereof by administering (preferably orally) an effective amount of the composition of the present invention. Preferably the composition (e.g., 80 mg/kg/day of acyclovir or a molar equivalent of a salt or prodrug thereof) is administered every 5 or more hours and less than 4 times daily. For children (2 years of age and older), an amount of the composition can be orally administered to provide the equivalent bioavailability as 20 mg/kg per dose 4 times daily of the current acyclovir formulations marketed as Zovirax® (U.S. FDA NDA No. 18828, 19909, or 20089). For adults or children over 40 kg, an amount of the composition can be orally administered to provide the equivalent bioavailability as 800 mg of the current acyclovir formulations marketed as Zovirax® (U.S. FDA NDA No. 18828, 19909, or 20089) administered 4 times daily.

Yet another embodiment is a method of preparing a composition of the present invention by mixing at least one delivery agent compound and acyclovir or a salt, ester, or prodrug thereof.

DETAILED DESCRIPTION OF THE INVENTION

Definitions

The term "hydrate" as used herein includes, but is not limited to, (i) a substance containing water combined in the molecular form and (ii) a crystalline substance containing one or more molecules of water of crystallization or a crystalline material containing free water.

The term "solvate" as used herein includes, but is not limited, to, a molecular or ionic complex of molecules or ions of a solvent with molecules or ions of the delivery agent compound or salt thereof, or hydrate or solvate thereof.

The term "delivery agent" refers to any of the delivery agent compounds disclosed herein.

The term "SNAC" refers to the monosodium salt of N-(8-[2-hydroxybenzoyl]-amino)caprylic acid, unless otherwise indicated. Unless otherwise noted, the team "SNAC" refers to all forms of SNAC, including all amorphous and polymorphic forms of SNAC, such as SNAC trihydrate and those described in U.S. Ser. Nos. 60/619,418 and 60/569,476, both of which are hereby incorporated by reference. The term "SNAC trihydrate" as used herein refers to a crystalline form of SNAC in which three molecules of water are associated with each molecule of SNAC. SNAC can be prepared by the procedures described in U.S. Pat. No. 5,650,386 and international Publication Nos. WO00/46182 and WO00/59863.

The term "SNAD" refers to the monosodium salt of N-(10-[2-hydroxybenzoyl]-amino)decanoic acid, unless otherwise indicated. The term "disodium salt of SNAD" refers to the disodium salt of N-(10-[2-hydroxybenzoyl]-amino)decanoic acid.

An "effective amount of acyclovir" is an amount of acyclovir which is effective to treat or prevent a condition in a living organism to whom it is administered over some period of time, e.g., provides a therapeutic effect during a desired dosing interval.

An "effective amount of delivery agent" is an amount of the delivery agent which enables and/or facilitates the absorption of a desired amount of acyclovir via any route of administration (such as those discussed in this application including, but not limited to, the oral (e.g., across a biological membrane in the gastrointestinal tract), nasal, pulmonary, dermal, buccal, vaginal, and/or ocular route).

The term "mean", when preceding a pharmacokinetic value (e.g., mean Peak) represents the arithmetic mean value of the pharmacokinetic value unless otherwise specified.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "about" generally means within 10%, preferably within 5%, and more preferably within 1% of a given value or range.

The terms "alkyl" and "alkenyl" as used herein include linear and branched alkyl and alkenyl substituents, respectively.

The phrase "pharmaceutically acceptable" refers to additives or compositions that are physiologically tolerable and do not typically produce an allergic or similar untoward reaction, such as gastric upset, dizziness and the like, when administered to a mammal.

By "condition or disorder caused by a virus" is meant any condition or disorder in an animal that is either caused by, complicated by, or aggravated by a virus. Such conditions or disorders include, but are not limited to, those caused by viruses of the herpes family, for example, herpes simplex 1 and 2 viruses (HSV 1, HSV 2), varicella zoster virus (VZV), cytomegalovirus (CMV), Epstein-Barr virus (EBV), and other herpes virus infections (e.g. feline herpes virus infections).

As used herein, the term "treat" includes one or more of the following:

(a) arresting, delaying the onset (i.e., the period prior to clinical manifestation of a disorder and/or reducing the risk of developing or worsening a disorder;

(b) relieving or alleviating at least one symptom of a disorder in a mammal, including for example, hypercalcemia; or

(c) relieving or alleviating the intensity and/or duration of a manifestation of a disorder experienced by a mammal including, but not limited to, those which are in response to a given stimulus (e.g., pressure, tissue injury or cold temperature). The term "treat" also includes prophylactically preventing, curing, healing, alleviating, relieving, altering, remedying, ameliorating, improving, or affecting a condition (e.g., a disease), the symptoms of the condition, or the predisposition toward the condition.

Acyclovir

The term "acyclovir" refers to 9-(2-hydroxyethoxymethyl)guanine. Suitable salts (e.g., pharmaceutically acceptable salts) and esters of acyclovir are described in U.S. Pat. No. 4,199,574, which is hereby incorporated by reference, and include, but are not limited to, sodium acyclovir and acyclovir valerate. Acyclovir also forms acid addition salts, such as with hydrochloric, sulphuric, phosphoric, maleic, fumaric, citric, tartaric, lactic and acetic acid.

A synthesis of acyclovir is disclosed in U.S. Pat. No. 4,199,574, which is hereby incorporated by reference. Acyclovir is commercially available from GlaxoSmithKline (Research Triangle Park, N.C.) under the tradename Zovirax™.

Any prodrug which is converted in vivo to 9-(2-hydroxyethoxymethyl)guanine can also be used. The term "prodrug" as used herein includes pharmaceutically acceptable salts of the drug. Acyclovir prodrugs include, substituted purines of the formula:

or salts thereof, wherein:

R is hydrogen, hydroxy, or amino;

X is oxygen or sulphur;

Y is hydrogen or hydroxymethyl; and

Z is —H, $C_{1-16}$ alkyl, or —OCOCH($R_1$)NH$_2$, wherein $R_1$ is —CH[CH$_3$]$_2$.

Suitable acyclovir prodrugs, include but are not limited to, those described in U.S. Pat. Nos. 4,609,662, 4,758,572 and 4,957,924, all of which are hereby incorporated by reference. A non-limiting example of such a prodrug is 2-[(2-amino-1,6-dihydro-6-oxo-9H-purin-9-yl)methoxy]ethyl ester (valacyclovir) and its pharmaceutically acceptable salts. Valacyclovir is commercially available as its hydrochloride salt from GlaxoSmithKline (Research Triangle Park, N.C.) under the tradename Valtrex™.

Therapeutically effective amounts of a acyclovir for use in treatment of all conditions and disorders described, herein, is an amount sufficient to suppress or alleviate conditions associated with the viral infection. As will be recognized by those in the field, an effective amount of therapeutic agent will vary with many factors including the potency of the acyclovir or salt, ester, or prodrug thereof, the age and weight of the patient, and the severity of the condition or disorder to be treated.

According to one embodiment, the acyclovir (or a salt, ester, prodrug thereof) is administered (e.g. peripherally) at a dose of about 0.1 to about 250 mg per kilogram of body weight of the recipient per day (mg/kg/day), about 1 to about 100 mg/kg/day, or about 5 to about 20 mg/kg/day (based on the weight of acyclovir). According to another embodiment, the dose is about 10 mg/kg/day. The desired dose may be administered either as a single or divided dose.

The acyclovir and delivery agent compound may be administered separately or together with one or more other active agents. For example, the acyclovir and delivery agent compound may be administered separately or together with compounds or compositions that exhibit antiviral activity, such as compounds used to treat retroviral infections (particularly HIV infections), e.g., 3'-azido-3'-deoxythymidine (AZT) and/or compounds or compositions that exhibit activity as ribonucleotide reductase inhibitors. Suitable ribonucleotide reductase inhibitors include, but are not limited to, thiocarbonohydrazone ribonucleotide reductase inhibitors, such as those disclosed in U.S. Pat. No. 5,393,883, which is hereby incorporated by reference.

Delivery Agent Compounds

The delivery agent compound may be any of those described in U.S. Pat. Nos. 6,699,467, 6,663,898, 6,693,208, 6,693,073, 6,693,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 6,100,298, 6,100,285, 6,099,856, 6,090,958, 6,084,112, 6,071,510, 6,060,513, 6,051,561, 6,051,258, 6,001,347, 5,990,166, 5,989,539, 5,976,569, 5,972,387, 5,965,121, 5,962,710, 5,958,451, 5,955,503, 5,939,381, 5,935,601, 5,879,681, 5,876,710, 5,866,536, 5,863,944, 5,840,340, 5,824,345, 5,820,881, 5,811,127, 5,804,688, 5,792,451, 5,776,888, 5,773,647, 5,766,633, 5,750,147, 5,714,167, 5,709,861, 5,693,338, 5,667,806, 5,650,386, 5,643,957, 5,629,020, 5,601,846, 5,578,323, 5,541,155, 5,540,939, 5,451,410, 5,447,728, 5,443,841, and 5,401,516; International Publication Nos. WO94/23767, WO95/11690, WO95/28920, WO95/28838, WO96/10396, WO96/09813, WO96/12473, WO97/36480, WO 2004/4104018, WO 2004080401, WO 2004062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/06534, WO 00/06184, WO 00/59863, WO 00/59480, WO 00/50386, WO 00/48589, WO 00/47188, WO 00/46182, WO 00/40203, WO 99/16427, WO 98/50341, WO 98/49135, WO 98/34632, WO 98/25589, WO 98/2.1951, WO 97/47288, WO 97/31938, WO 97/10197, WO 96/40076, WO 96/40070, WO 96/39835, WO 96/33699, WO 96/30036, WO 96/21464, WO 96/12475, and WO 96/12474; and U.S. Published Application Nos. 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 200201.02286, 20020065255, 20020052422, 20020040061, 20020028250, 20020013497, 20020001591, 20010039258, and 20010003001. Each of the above listed U.S. patents and U.S. and International published applications are herein incorporated by reference.

Non-limiting examples of delivery agent compounds include N-(8-[2-hydroxybenzoyl]-amino)caprylic acid, N-(10-[2-hydroxybenzoyl]-amino)decanoic acid, 8-(2-hydroxy-4-methoxybenzoylamino)octanoic acid, 8-(2,6-dihydroxybenzoylamino)octanoic acid, 8-(2-hydroxy-5-bromobenzoylamino)octanoic acid, 8-(2-hydroxy-5-chlorobenzoylamino)octanoic acid, 8-(2-hydroxy-5-iodobenzoylamino)octanoic acid, 8-(2-hydroxy-5-methylbenzoylamino)octanoic acid, 8-(2-hydroxy-5-fluorobenzoylamino)octanoic acid, 8-(2-hydroxy-5-methoxybenzoylamino)octanoic acid, 8-(3-hydroxyphenoxy)octanoic acid, 8-(4-hydroxyphenoxy)octanoic acid, 6-(2-cyanophenoxy)hexanoic acid, 8-(2-Hydroxyphenoxy)octyl-diethanolamine, 8-(4-hydroxyphenoxy)octanoate, 8-(4-hydroxyphenoxy)octanoate, 8-(2-hydroxy-4-methoxybenzoylamino)octanoic acid, 8-(2-hydroxy-5-methoxybenzoylamino)octanoic acid, and salts thereof. Preferred salts include, but are not limited to, monosodium and disodium salts.

The delivery agent compounds may be in the form of the carboxylic acid or pharmaceutically acceptable salts thereof, such as sodium salts, and hydrates and solvates thereof. The salts may be mono- or multi-valent salts, such as monosodium salts and disodium salts. The delivery agent compounds may contain different counter ions chosen for example due to their effect on modifying the dissolution profile of the carrier.

The delivery agent compounds may be prepared by methods known in the art, such as those discussed in the aforementioned publications (e.g., International Publication Nos. WO 98/34632, WO 00/07979, WO 01/44199, WO 01/32596, WO 02/20466, and WO 03/045306). SNAC, SNAD, and the free acid and other salts thereof may be prepared by methods known in the art, such as those described in U.S. Pat. Nos. 5,650,386 and 5,866,536.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Delivery Systems

The composition of the present invention comprises one or more delivery agent compounds of the present invention and acyclovir. The delivery agent compound and acyclovir are typically mixed prior to administration to form an administration composition.

The administration compositions may be in the form of a liquid. The solution medium may be water, 25% aqueous propylene glycol, or phosphate buffer. Other dosing vehicles include polyethylene glycol. Dosing solutions may be prepared by mixing a solution of the delivery agent compound with a solution of the active agent, just prior to administration. Alternately, a solution of the delivery agent compound (or acyclovir) may be mixed with the solid form of acyclovir (or delivery agent compound). The delivery agent compound and acyclovir may also be mixed as dry powders. The delivery agent compound and acyclovir can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

For example, the compositions useful in the invention can be provided as parenteral compositions (e, g., injection or infusion). According to one embodiment, the composition is suspended in an aqueous carrier, such as in an isotonic buffer solution at a pH of about 3.0 to about 8.0. Suitable buffers include, but are not limited to, sodium citrate-citric acid and sodium phosphate-phosphoric acid, and sodium acetate/acetic acid buffers.

A form of repository or "depot" slow release preparation may also be used so that therapeutically effective amounts of the preparation are delivered into the bloodstream over many hours or days following transdermal injection or delivery.

The administration compositions may alternately be in the form of a solid, such as a tablet, capsule or particle, such as a powder or sachet. Solid dosage forms may be prepared by mixing the solid form of the compound with the solid form of acyclovir. Alternately, a solid may be obtained from a solution of compound and acyclovir by methods known in the art, such as freeze-drying (lyophilization), precipitation, crystallization and, solid dispersion. Alternatively, the administration can be a semi-solid, in the form of a gel, paste, colloid, gelatin, emulsion, suspension and the like.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of acyclovir used in an administration composition of the present invention is an amount effective to treat the target indication. However, the amount can be less than that amount when the composition is used in a dosage unit form because the dosage unit form may contain a plurality of delivery agent compound/acyclovir, such compositions may contain a divided effective amount. The total effective amount can then be administered in cumulative units containing, in total, an effective amount of acyclovir. Moreover, those skilled in the filed will recognize that an effective amount of acyclovir will vary with many factors including the age and weight of the patient, the patient's physical condition, as well as other factors.

The total amount of acyclovir to be used of can be determined by methods known to those skilled in the art. However, because the compositions of the invention may deliver acyclovir more efficiently than compositions containing acyclovir lower amounts of acyclovir than those used in prior dosage unit forms or delivery systems can be administered to the subject, while still achieving the same blood levels and/or therapeutic effects.

According to one embodiment, the acyclovir (or a salt, ester, prodrug thereof) is administered (e.g. peripherally) at a dose of about 0.1 to about 250 mg per kilogram of body weight of the recipient per day (mg/kg/day), about 1 to about 100 mg/kg/day, or about 5 to about 20 mg/kg/day (based on the weight of acyclovir). According to another embodiment, the dose is about 10 mg/kg/day. The desired dose may be administered either as a single or divided dose.

The present invention also includes pharmaceutical compositions and dosage forms which include the aforementioned amounts of acyclovir and at least one delivery agent Generally an effective amount of delivery agent to facilitate the delivery acyclovir is administered with acyclovir. According to one embodiment, the amount of delivery agent to acyclovir on a molar basis ranges from about 20:1 to about 1:1, from about 10:1 to about 2:1, or from about 5:1 to about 2:1.

The presently disclosed delivery agent compounds facilitate the delivery of acyclovir, particularly in oral, intranasal, sublingual, intraduodenal, subcutaneous, buccal, intracolonic, rectal, vaginal, mucosal, pulmonary, transdermal, intradermal, parenteral, intraperitoneal, intravenous, intramuscular and ocular systems, as well as traversing the blood-brain brain barrier. The compositions and dosage unit forms of the present invention can be administered by any of the aforementioned routes.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compositions of the subject invention are useful for administering biologically or chemically active agents to any animals, including but not limited to birds such as chickens; fish, reptiles, mammals, such as rodents, cows, pigs, dogs, cats, primates, and particularly humans, and insects.

Methods of Treatment

The composition of the present invention can treat any disorder which is treatable with acyclovir or its salts (e.g., acyclovir sodium) or prodrugs (e.g., valacyclovir), including those described in the *Physicians' Desk Reference* (58$^{th}$ Ed., 2004, Medical Economics Company, Inc., Montvale, N.J.). Such disorders include, but are not limited to, those described above or in the patents or other publications above. Non-limiting examples are:
 (1) herpes simplex 1 virus (HSV 1),
 (2) herpes simplex 2 virus (HSV 2),
 (3) varicella zoster virus (VZV),
 (4) cytomegalovirus (CMV),
 (5) Epstein-Barr virus (EBV),
 (6) other herpes virus infections (e.g. feline herpes virus infections),
 (7) herpetic karatitis,
 (8) herpetic encapalitis,
 (9) cold sores and genital infections (caused by herpes simplex),
 (10) chicken pox,
 (11) shingles (caused by varicella zoster),
 (12) CMV-pneumonia and retinitis, particularly in immunocompromised patients including renal and bone marrow transplant patients and patients with Acquired Immune Deficiency Syndrome (AIDS),
 (13) Epstein-Barr virus (EVB) caused infectious mononucleosis, nasopharyngeal cancer, immunoblastic lymphoma, Burkitt's lymphoma and hairy leukoplakia,
 (14) herpes zoster, and
 (15) initial episodes and/or the management of recurrent episodes of genital herpes.

EXAMPLES

The following examples illustrate the invention without limitation. All parts are given by weight unless otherwise indicated.

Example 1

Solid Oral Delivery of Acyclovir in Rats

The dose of Acyclovir used was 25 mg/kg body weight. The dose of delivery agent was either 50 or 75 mg/kg body weight.

Approximately 6.25 mg/tablet of acyclovir was blended with either 12.5 or 18.75 mg/tablet (50 and 75 mg/kg, respectively) of delivery agent compound. Upper punch, lower punch and die of a Carver 4350 manual pellet press with a Caplet shape model sold by Natoli Engineering Company, Inc. were treated with magnesium stearate (0.1%). Approximately 6.25 mg (Acyclovir alone), 18.75 mg (Acyclovir+50 mg/kg delivery agent compound), or 25 mg (Acyclovir+75 mg/kg delivery agent compound) of mixed powder was fed into the die and a mini bead shape tablet was made at about 1000 PSI bar pressure. The resulting solid dosage forms were 2.65 mm in diameter and approximately 8.40 mm in length for the 25 mg tablets, 6.3 mm in length for the 18.75 mg tablets, and 2.1 mm in length for the 6.25 mg tablets.

Male Sprague Dawley rats (~250 g) were fasted overnight and then anesthetized by standard $CO_2$ inhalation technique for approximately 10 seconds, resulting in an anesthetized state for less then one minute.

An oral dosing tube was used. The dosing tube was inserted into the rat's mouth and carefully threaded down the pharynx and esophagus about 8 cm to about 15 cm depending on the weight of the rat (typically about 11 cm). The solid dosage form was delivered into the distal esophagus and/or stomach by pressing the plunger of the oral dosing tube.

Figure 1:
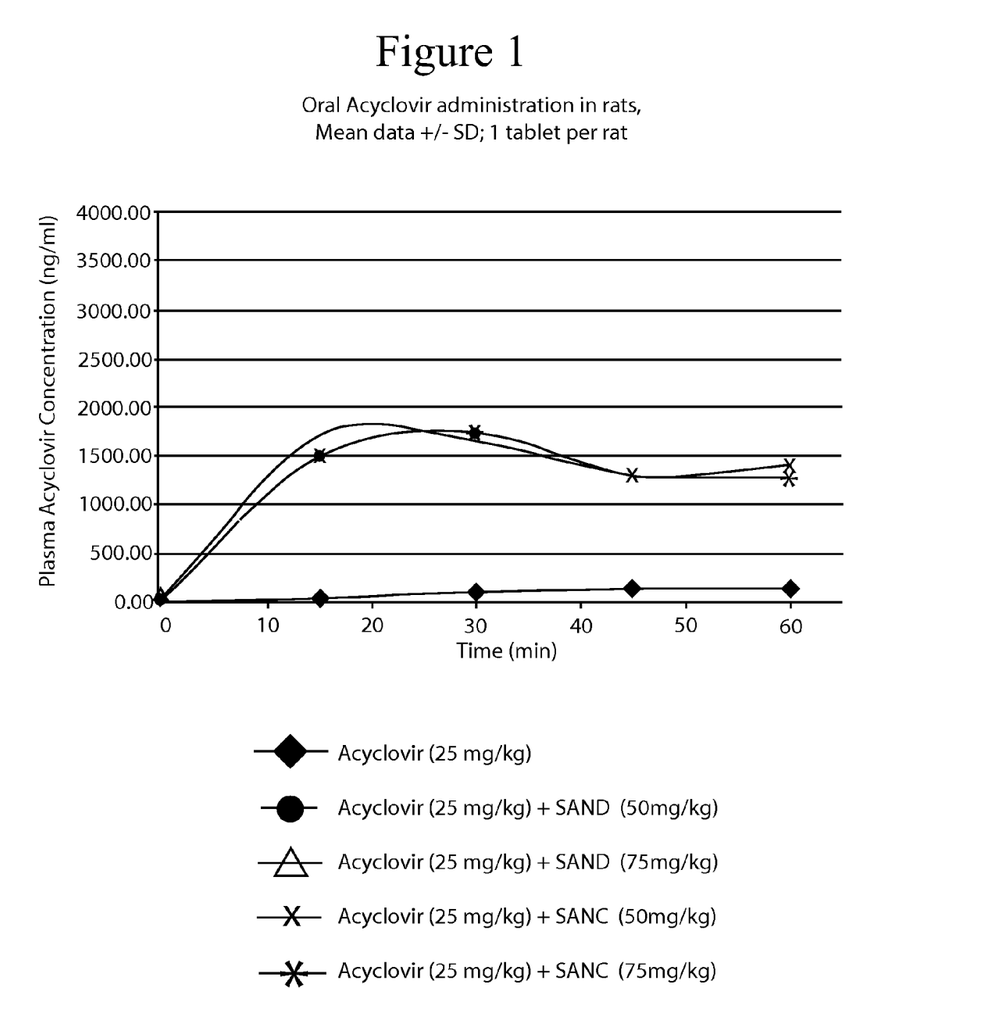
FIG. 1 is a graph of the serum concentrations (ng/ml±standard error) of acyclovir versus time after oral administration with and without the delivery agent SNAC or SNAD by the procedure described in Example 1.
Figure 2:
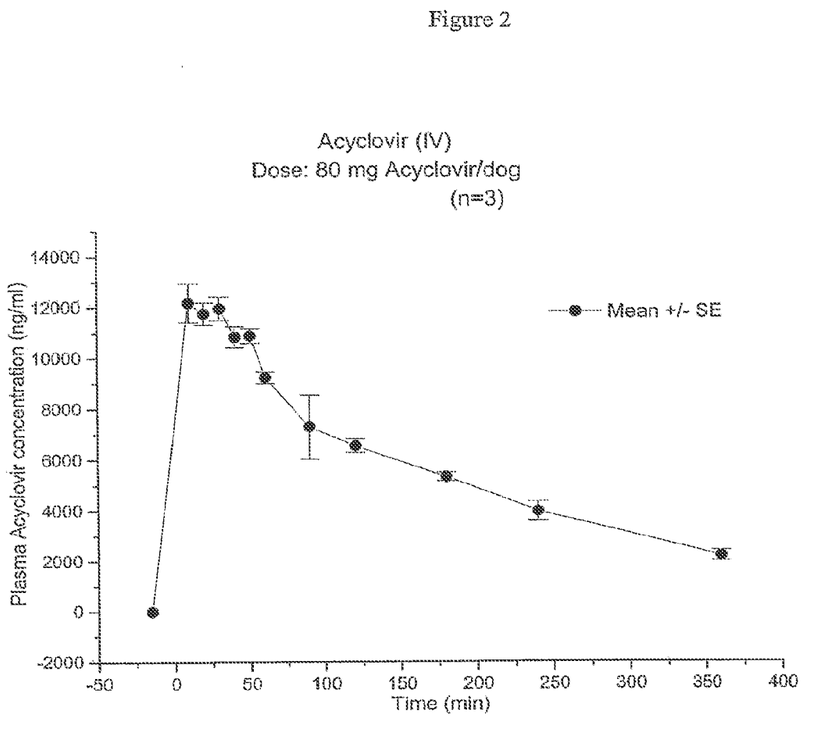
FIGS. 2, 4, and 6-10 are graphs of the serum concentrations (ng/ml standard error) of acyclovir versus time after intravenous or oral administration with or without the delivery agent SNAC of formulations 1, 3, and 5-9 shown in table 2, respectively, by the procedure described in Example 2.
Figure 3:
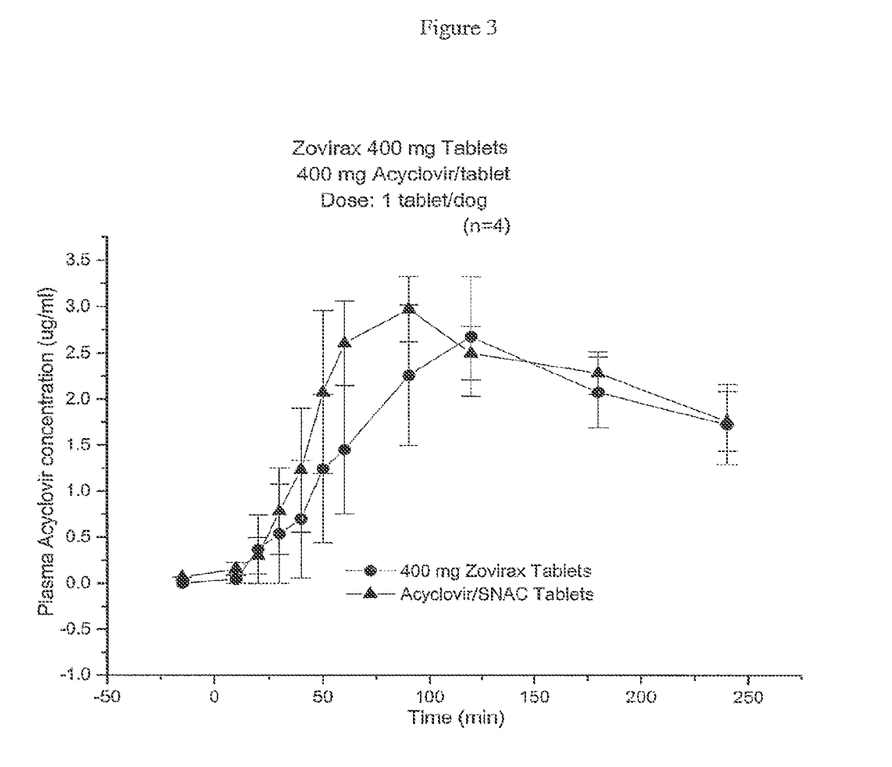
FIG. 3 shows graphs of the serum concentrations (ng/ml±standard error) of acyclovir versus time after oral administration of (1) 400 mg of acyclovir (without a delivery agent) of formulation 5 (shown in table 2) or (2) 80 mug of acyclovir and 240 mg of the delivery agent SNAC of formulation 2 (shown in table 2), respectively, by the procedure described in Example 2.
Figure 4:
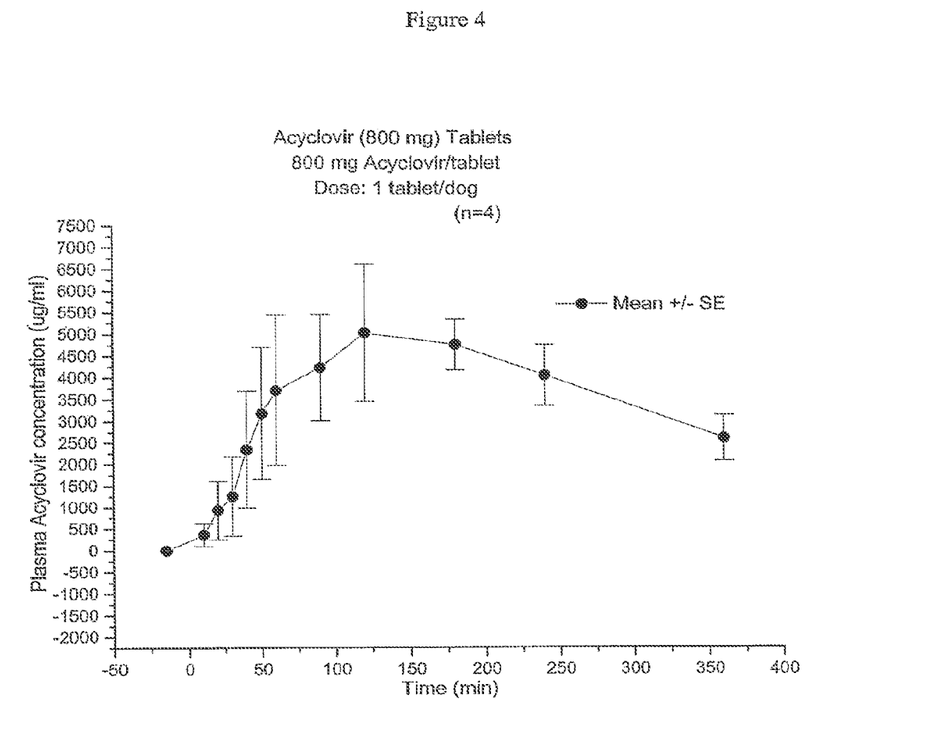
Figure 5:
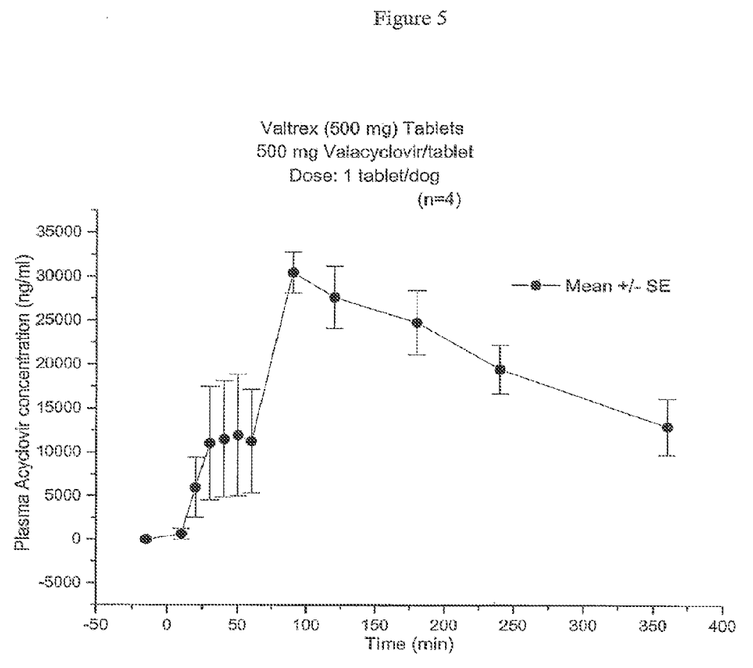
FIG. 5 is a graph of the serum concentration (ng/ml±standard error) of acyclovir versus time after oral administration of valacyclovir (without a delivery agent) of formulation 4 shown in table 2, respectively, by the procedure described in Example 2.
Figure 6:
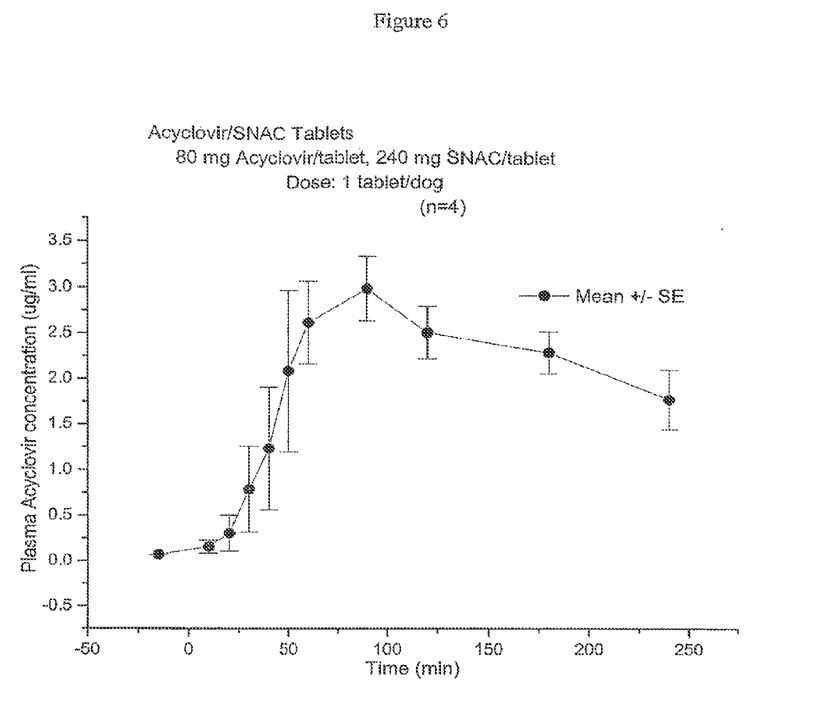
Figure 7:
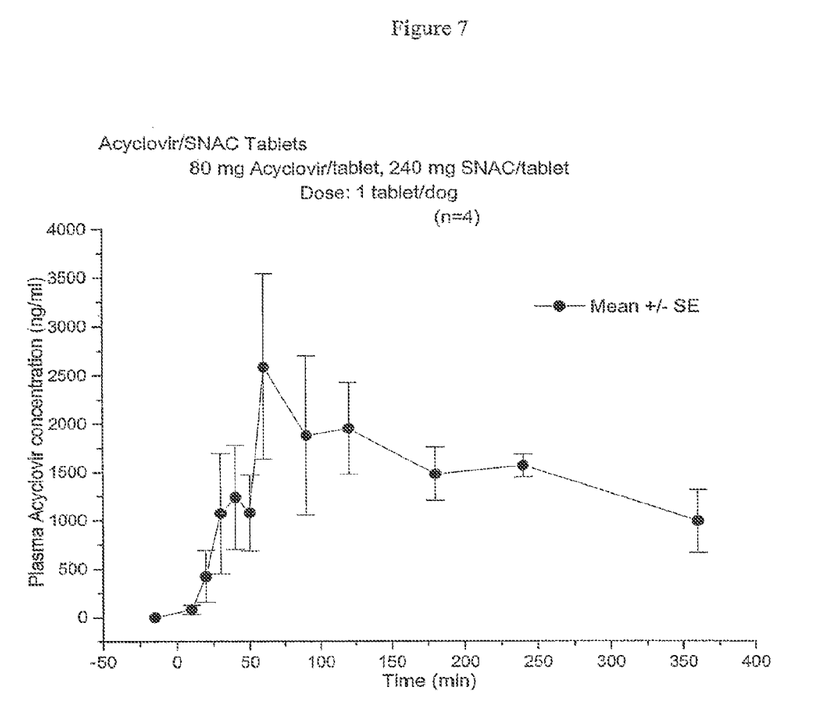
Figure 8:
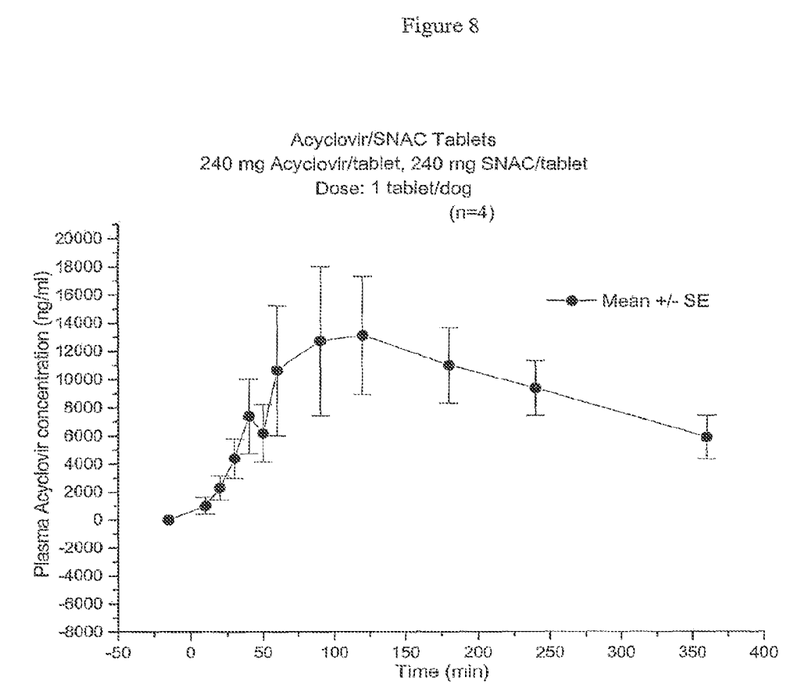
Figure 9:
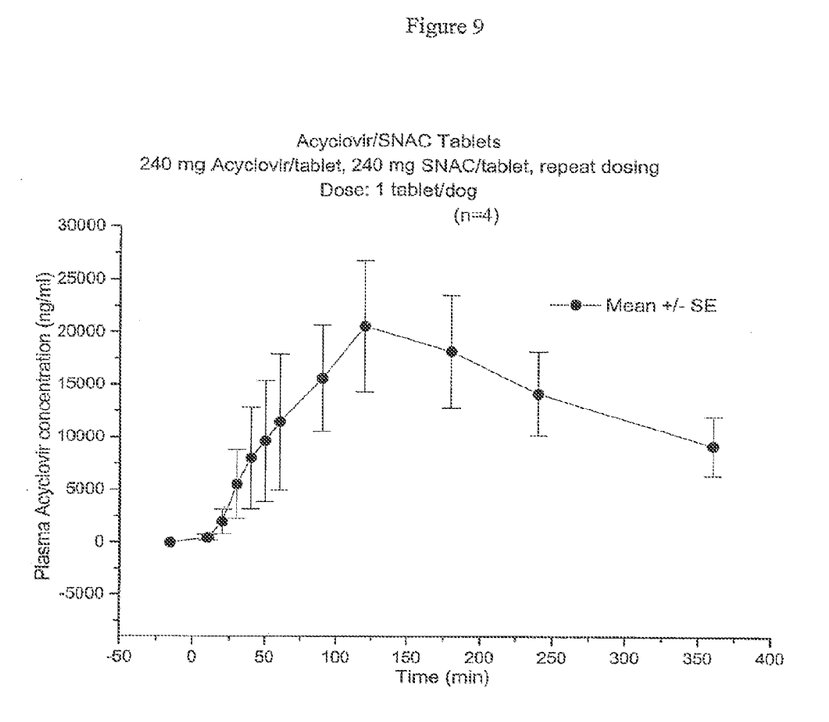
Figure 10:
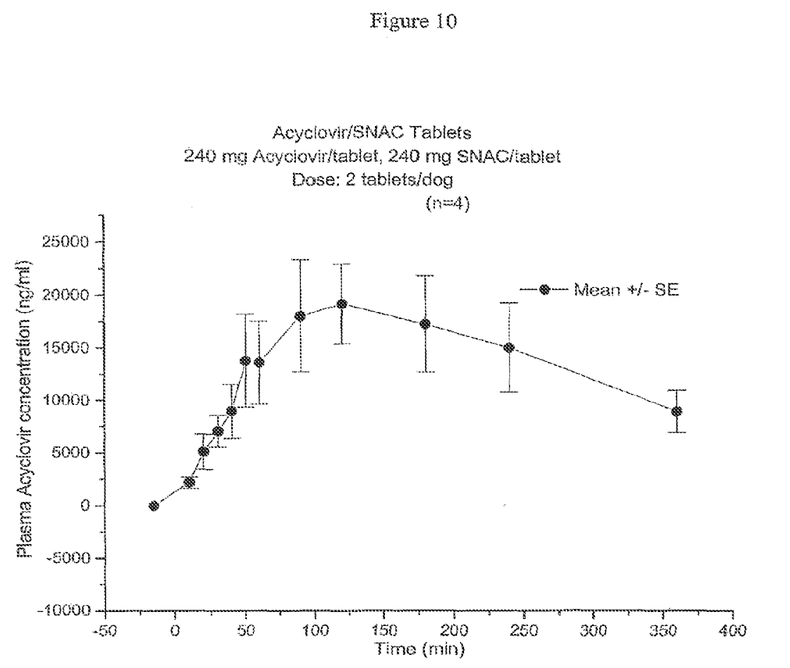

Blood samples were collected serially from the retro-orbital sinus at 0, 15, 30, 45, and 60 minutes. Samples were collected on wet ice into heparin-containing tubes. Samples were centrifuged and plasma was extracted. Plasma samples were stored in a −20° C. freezer until analysis. Plasma Acyclovir concentrations were quantified using a LC-MS-MS method (analysis performed by Quest Pharmaceutical Services, Newark, Del.). Results from the animals in each group were averaged for each time point. The maximum of these averages (i.e., the mean peak plasma Acyclovir concentration±standard deviation (SD)) is reported below in Table 1. The results are also shown in FIG. 1,

TABLE 1

Oral Delivery of Acyclovir in Rats

| Delivery Agent | Delivery Agent dose (mg/kg) | Acyclovir (mg/kg) | Mean plasma peak of Acyclovir (ng/ml) ± SD |
|---|---|---|---|
| None | — | 25 | 95.11 ± 73.75 |
| 1 | 50 | 25 | 1719.32 ± 676.52 |
| 1 | 75 | 25 | 2759.93 ± 1699.39 |
| 2 | 50 | 25 | 778.12 ± 491.9 |
| 2 | 75 | 25 | 1694.65 ± 1133.57 |

Delivery Agent 1 is the monosodium salt of N-(8-[2-hydroxybenzoyl]-amino)caprylic acid (SNAC).
Delivery Agent 2 is the monosodium salt of N-(10-[2-hydroxybenzoyl]-amino)decanoic acid (SNAD).

Example 2

Delivery of Acyclovir in Dogs

Six different oral dosage forms (tablets) were administered to dogs; (1) unitary solid oral dosage forms comprising 80 mg of acyclovir and 240 mg of the delivery agent, the monosodium salt of N-(8-[2-hydroxybenzoyl]-amino)caprylic acid (SNAC), (2) a solid oral dosage form comprising 400 mg of acyclovir (Zovirax™, commercially available from GlaxoSmithKline), (3) a solid oral dosage form comprising 800 mg dosage of (Zovirax™, commercially available from GlaxoSmithKline), (4) a solid oral dosage form comprising 500 mg dosage of valacyclovir (Valtrex™, commercially available from GlaxoSmithKline) and (6) unitary solid oral dosage comprising 240 mg of acyclovir and 240 mg of the delivery agent SNAC. Oral administration of acyclovir alone and with a delivery agent was compared to an interveneous dosage form comprising 80 mg of acyclovir (Zovirax™ for injection, commercially available from GlaxoSmithKline).

Unitary dosages of acyclovir and delivery agent were prepared as follows. Approximately 240 mg/tablet of SNAC was blended with either 80 or 240 mg/tablet of acyclovir. Upper punch, lower punch and die of a Carver 4350 manual pellet press with a Caplet shape model sold by Natoli Engineering Company, Inc. were treated with magnesium stearate (0.1%). Approximately 320 mg (80 mg acyclovir and 240 mg SNAC), or 480 mg (240 mg acyclovir and 240 mg SNAC) of mixed powder was fed into the die and a mini bead shape tablet was made at about 1000 PSI bar pressure.

Each dog was dosed as described in Table 2. Plasma acyclovir concentrations were quantified using a LC-MS-MS method. The maximum peak plasma acyclovir concentration and the area under the curve (AUC) are reported below in Table 2. The results for experiments 1-9 are also shown in FIGS. 2-10, respectively,

TABLE 2

Delivery of Acyclovir in Dogs

| Formulation No. | Route of Administration | Delivery Agent (mg) | Acyclovir (mg) | Mean plasma peak of Acyclovir (ng/ml) | AUC (ng/ ml*min) |
|---|---|---|---|---|---|
| 1 (n = 3) | Intravenous | — | 80 | 12186 | 2177300 |
| 2 (n = 4) | Oral | — | 400 | 2685 | 423925 |
| 3 (n = 4) | Oral | — | 800 | 5029 | 1317130 |
| 4 (n = 4) | Oral | — | 500[1] (valacyclovir) | 30516 | 6822910 |
| 5 (n = 4) | Oral | 240 | 80 | 2982 | 492338 |
| 6 (n = 4) | Oral | 240 | 30 | 2592 | 525056 |
| 7 (n = 4) | Oral | 240 | 240 | 13142 | 3268320 |
| 8 (n = 4) | Oral | 240 | 240 | 20591 | 4811610 |
| 9 (n = 4) | Oral | 480[2] | 480[2] | 19144 | 4988940 |

[1]Delivered as valacyclovir (Valtrex ™, commercially available from GlaxoSmithKline)
[2]Delivered as two tablets comprising 240 mg Acyclovir and 240 mg of delivery agent The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

We claim:

1. A solid oral pharmaceutical composition comprising (a) acyclovir and (b) a delivery agent of the formula or a salt thereof, wherein:

Ar is 2-hydroxyphenyl or 2-hydroxynaphthyl;
Ar is optionally further substituted with one or more of —OH, halogen, $C_1$-$C_4$ alkyl, $C_1$-$C_4$ alkenyl, $C_1$-$C_4$ alkoxy or $C_1$-$C_4$ haloalkoxy;
$R^7$ is $C_6$-$C_{10}$ alkyl; and
$R^8$ is hydrogen.

2. A pharmaceutical composition of claim 1, wherein the delivery agent is selected from the group consisting of (8-[2-hydroxybenzoyl]-amino)caprylic acid, N-(10-[2-hydroxybenzoyl]-amino)decanoic acid or a pharmaceutically acceptable salt thereof.

3. The pharmaceutical composition of claim 1 wherein the delivery agent is N-(8-[2-hydroxybenzoyl]-amino)caprylic acid or a pharmaceutically acceptable salt thereof.

4. A dosage unit form comprising:
(A) the solid oral pharmaceutical composition of claim 1; and
(B)
  (a) an excipient,
  (b) a diluent,
  (c) a disintegrant,
  (d) a lubricant,
  (e) a plasticizer,
  (f) a colorant, or
  (g) any combination thereof.

5. The dosage unit form of claim 4, wherein the dosage unit form is in the form of a tablet, a capsule, a particle, a powder, a sachet, or a liquid.

6. The dosage unit form of claim 4, wherein the dosing vehicle is a liquid selected from the group consisting of water, aqueous propylene glycol, phosphate buffer, 1,2-propane diol, ethanol, and any combination thereof.

7. A method for administering an effective amount of acyclovir a patient in need of thereof, comprising the step of orally administering the pharmaceutical composition of claim 1.

8. A method of treating a viral infection in a patient in need thereof, comprising the step of orally administering to the patient an effective amount of the pharmaceutical composition of claim 1.

9. A method of treating a condition or disorder caused by a virus in a patient in need thereof, comprising the step of orally administering an animal an effective amount of the pharmaceutical composition of claim 1.

10. The method of claim 9, wherein the condition or disorder is caused by a virus selected from the group consisting of herpes simplex 1, herpes simplex 2, varicella zoster virus, cytomegalovirus and Epstein-Barr virus.

11. A method of improving the bioavailability of acyclovir in an animal in need thereof, the method comprising the step of orally administering a formulation of claim 1.

* * * * *